United States Patent
Kodama et al.

(10) Patent No.: US 6,828,298 B2
(45) Date of Patent: Dec. 7, 2004

(54) **GLYCOPROTEIN HAVING INHIBITORY ACTIVITY AGAINST *HELICOBACTER PYLORI* COLONIZATION**

(75) Inventors: Yoshikatsu Kodama, Gifu (JP); Nobutake Kimura, Saitama (JP)

(73) Assignees: Ghen Corporation, Gifu (JP); Nisshin Pharma Inc., Tokyo (JP)

( * ) Notice: Subject to any disclaimer, the term of this patent is extended or adjusted under 35 U.S.C. 154(b) by 0 days.

(21) Appl. No.: 09/833,637

(22) Filed: Apr. 13, 2001

(65) Prior Publication Data

US 2001/0044120 A1 Nov. 22, 2001

(30) Foreign Application Priority Data

Apr. 14, 2000 (JP) ........................................ 2000-113913

(51) Int. Cl.⁷ ......................... A61K 38/16; A61K 49/00
(52) U.S. Cl. ........................... 514/8; 530/395; 530/413; 435/252.1; 424/9.1
(58) Field of Search .............................. 514/8; 530/413; 530/395; 435/252.1; 424/9.1

(56) References Cited

U.S. PATENT DOCUMENTS

| | | | |
|---|---|---|---|
| 5,116,821 A | 5/1992 | Randall et al. ............... 514/25 |
| 5,505,955 A | * 4/1996 | Peterson et al. ............ 424/439 |
| 6,235,709 B1 | * 5/2001 | Kodama et al. .............. 514/2 |

FOREIGN PATENT DOCUMENTS

| | | |
|---|---|---|
| JP | 10-287585 | 10/1998 |
| JP | 11-263731 | 9/1999 |

OTHER PUBLICATIONS

Hashimoto et al. (Digestive Disease and Sciences, 36, 888–892 (1991).*

Webb et al., "Fundamentals of Dairy Chemistry", 1988, Avi Publishing Co., Westport, Ct., Abstract No. XP002195230, pp. 103–105.

Shauer, "Novel infection protection agent against *Helicobacter pylori* microbe for pharmaceutical and food products—consists of iron bonding type lactoferrin active ingredient for opposing specific pylori microbe", 1999, Derwent Publications Ltd., London, England, Abstract No. XP002195231.

Snow Brand Milk Prod. Co. Ltd., "Agent for treating stomach and intestine—contains lactoferrin", 1998, Derwent Publications Ltd., London, England, Abstract No. XP002195232.

Icatlo et al., "Affinity Purification of *Helicobacter pylori* Unrease", *The Journal of Biological Chemistry*, 1988, pp. 18130–38, vol. 273, No. 29, John Wiley & Sons, New York, New York.

Yamazaki et al., "Antibacterial Effects of Lactoferrin and a Pepsin–Generated Lactoferrin Peptide against *Helicobacter pylori* in vitro," *Journal of Infect. Chemother.*, 1997, pp. 85–89, vol. 3.

Wada et al., "The Therapeutic Effect of Bovine Lactoferrin in the Host Infected with *Helicobater pylori*," *Scandinavian Journal of Gastroenterology*, 1999, pp. 238–243, vol. 34, No. 3.

Hirmo et al., "Inhibition of *Helicobacter pylori* sialic acid – specific haemagglutination by human gastrointestinal mucins and milk glycoproteins," *FEMS Immunology and Medical Microbiology*, 1998, pp. 275–281, vol. 20, No. 4, Elsevier Science B.V., Amsterdam, Netherlands.

Dial et al., "Antibiotic Properties of Bovine Lactoferrin on *Helicobacter pylori*," *Digestive Diseases and Sciences*, 1998, pp. 2750–2756, vol. 43, No. 12.

S. Hirmo et al., *FEMS Immunology and Medical Microbiology*, 20:275–81 (1998).

M. Clyne et al., *Infection and Immunity*, 61(10):4051–57 (1993).

* cited by examiner

*Primary Examiner*—Jon P. Weber
*Assistant Examiner*—Chih-Min Kam
(74) *Attorney, Agent, or Firm*—Burns, Doane, Swecker & Mathis, L.L.P.

(57) ABSTRACT

An inhibitor of *Helicobacter pylori* colonization in the stomach comprises as an active ingredient a glycoprotein which specifically binds to *H. pylori* urease. This glycoprotein is isolated and purified from a glycoprotein-containing substance, especially that derived from bovine milk whey or albumen of chicken eggs by affinity chromatography using a column on which *H. pylori* urease is immobilized. The glycoprotein is able to effectively inhibit *H. pylori* colonization, so is useful for the prevention or treatment of diseases caused by infection of *H. pylori* such as peptic ulcers. A food and medicament comprising the inhibitor are also provided.

16 Claims, 3 Drawing Sheets

GLYCOPROTEIN HAVING INHIBITORY ACTIVITY AGAINST *HELICOBACTER PYLORI* COLONIZATION

TECHNICAL FIELD

The present invention relates to a glycoprotein which is capable of eradicating from the stomach *Helicobacter pylori*, which is associated with the occurrence of peptic ulcers. It also relates to an inhibitor of the colonization of *Helicobacter pylori* comprising the glycoprotein, and a medicament and food comprising the inhibitor.

BACKGROUND OF THE INVENTION

At present it is believed that eradication of *H. pylori* from the stomach is essential for fully treating peptic ulcers. The combination of an antibiotic and an inhibitor of gastric acid secretion has been generally proposed as a therapy for eradication of *H. pylori* as described below.

*H. pylori* is a gram-negative spiral rod-shaped bacterium having flagella at one end and colonizing the human gastric mucosa. B. J. Marshall and J. R. Warren in Australia reported in 1983 that this bacterium was frequently detected in stomach biopsy specimens from patients with gastritis or gastric ulcers. At that time, this bacterium was named *Campylobacter pylori* since it resembles Campylobacter in morphology and growth characteristics. Later, it was found that the bacterium is different from Campylobacter in the fatty acid composition of its outer membrane and sequence of ribosome 16S-RNA. Therefore, the bacterium is now referred to as *Helicobacter pylori* and belongs to the newly established genus of Helicobacter.

Since then, many reports have been published based on epidemiological studies, indicating that this bacterium causes gastritis, gastric ulcers, and duodenal ulcers and is associated with diseases such as gastric cancer. Once *H. pylori* colonizes gastric mucosa, it survives and persists in the stomach and cannot be eradicated, although the immune response to infection thereof is strong, i.e., the antibody titer is high. Therefore, unless *H. pylori* is completely eliminated from the stomach by antibiotic therapy, the infection will return to the same level as before treatment within about a month after the administration of antibiotics is stopped. Additionally, the pH of the stomach is maintained very low by HCl, which is a strong acid, and therefore most antibiotics tend to be inactivated. For this reason, the combination of an antibiotic and a proton pump inhibitor which strongly suppresses the secretion of gastric acid is utilized for eradication of *H. pylori*.

However, the administration of antibiotics for a long time has the serious problems of increasing antibiotic-resistant strains as well as causing side effects.

Japanese Patent Application Kokai No. 11-263731 discloses that milk fat globule membrane fraction is effective for prevention of *H. pylori* infection. However, that publication merely teaches the ability to inhibit haemagglutination of *H. pylori* as evidence of prevention of *H. pylori* infection. Additionally, that publication states that milk fat globule membrane contains various components and does not state that which component is effective. Also, Sun Hirmo et al. states that gastric mucin and milk glycoprotein, specifically far globule membranes prepared from bovine buttermilk inhibit sialic acid-specific haemagglutination of *H. pylori* (FEMS Immunol. Medical Microbiology 20 (1998), pp. 275–281. However, it has been reported that there was no correlation between expression of haemagglutininins by *H. pylori* bacteria and the ability to bind gastric mucosa cells (M. Clyne & B. Drumm, Infection and Immunity, October 1993, pp. 4051–4057. Accordingly, the above-mentioned patent publication and article do not teach or suggest a substance which is capable of inhibiting the adherence of *H. pylori* to gastric mucosa.

Furthermore, the above patent publication and article have not elucidated an adhesin for adherence of *H. pylori* to gastric mucosa and a receptor therefor on gastric mucosa, which are important targets for inhibition of *H. pylori* infection.

SUMMARY OF THE INVENTION

It is an object of the present invention to provide an effective and safe inhibitor of *H. pylori* colonization which is associated with the occurrence of peptic ulcers, which inhibitor is capable of inhibiting the colonization of *H. pylori* effectively without the disadvantages of side effects and increase of drug-resistant strains which are associated with the use of antibiotics, and to provide a medicament and food useful for treating or preventing peptic ulcers.

Other objects and advantages as well as the nature of the present invention will be apparent from the following description.

Generally, the first step for establishment of an infection by a bacterium is adherence of the bacterium to a host cell and colonization of the bacterium by growing there. For the bacterium to adhere to the host cell, an adhesin has to bind to a receptor on the surface of the host cell. The specificity of the infective site of the bacterium is determined by this adhesin and the receptor. If the receptor molecule exists when the bacterium adheres to the host cell, competitive inhibition occurs and an infection is not established.

An adhesin of *H. pylori* and a receptor on human gastric mucosa are thought to be target molecules for inhibition of *H. pylori* infection. The present inventors clarified by studies on the mechanism of adherence of *H. pylori* that the adhesin of *H. pylori*, which had not been elucidated, is urease produced by *H. pylori* (Japanese Patent Application Kokai No. 10-287585).

The present inventors have studied substances capable of inhibiting the adherence of urease to gastric mucosa and have found that glycoproteins such as glycoprotein derived from the milk of a cow or glycoprotein derived from the albumen of a chicken egg are able to eliminate colonized *H. pylori* in the stomach by specifically binding to urease which is an adhesin localized on the surface layer of an *H. pylori* cell, and furthermore have found that the use of glycoprotein capable of specifically binding to urease even in a small amount, which glycoprotein is isolated and purified from these glycoprotein-containing substances by utilization of specific binding to urease, enables remarkably effective elimination of *H. pylori*.

According to the present invention, glycoprotein which is capable of specifically binding to urease is isolated and purified from a glycoprotein-containing substance by the affinity column technique which utilizes the specific binding to *H. pylori* urease, and the isolated and purified glycoprotein is used as an inhibitor of *H. pylori* colonization.

In one aspect, the present invention provides a glycoprotein which specifically binds to urease of *Helicobacter pylori* the glycoprotein being obtained by isolation and purification using a method utilizing specific adsorption to *Helicobacter pylori* urease.

In another aspect, the present invention provides an inhibitor of *Helicobacter pylori* colonization, comprising the above-mentioned glycoprotein as an active ingredient. The present invention also provides a pharmaceutical composition suitable for preventing or treating diseases caused by or associated with *Helicobacter pylori* in mammals including humans such as peptic ulcers, comprising the above-mentioned glycoprotein and a pharmaceutically acceptable carrier or diluent. Furthermore, the present invention provides a food which prevents or treats diseases caused by or associated with *Helicobacter pylori* in mammals including humans such as peptic ulcers when consumed in an effective amount, comprising the above-mentioned glycoprotein.

The method utilizing specific adsorption to *Helicobacter pylori* urease used in the present invention is preferably affinity chromatography using a column on which *Helicobacter pylori* urease is immobilized. The urease which is immobilized on the column may be recombinant urease.

DESCRIPTION OF THE PREFERRED EMBODIMENTS

Figure 1:
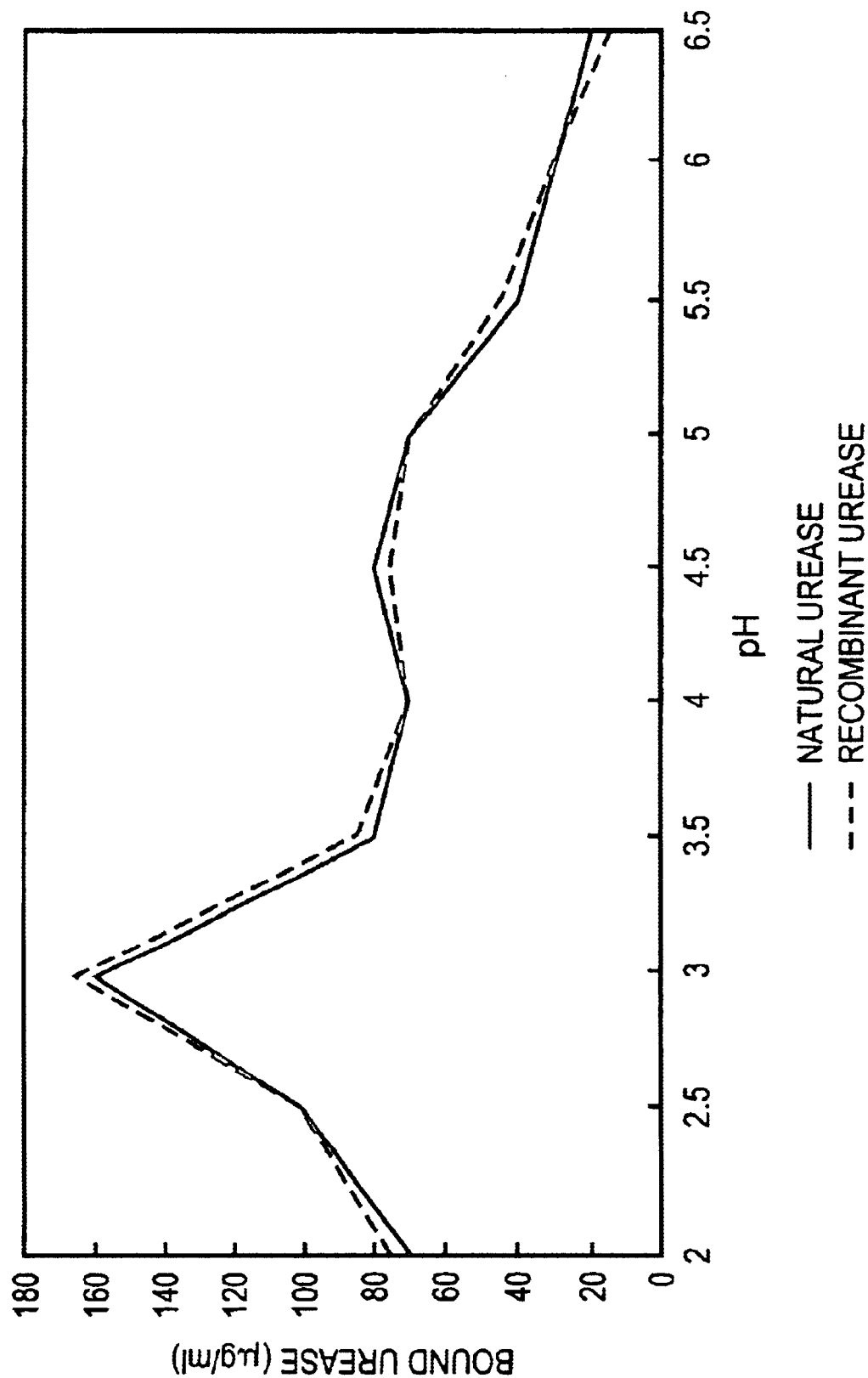
FIG. 1 is a graph showing adherence patterns of urease to purified porcine gastric mucin.

According to the present invention, a glycoprotein which specifically binds to urease is isolated and purified from a glycoprotein-containing substance by a method utilizing specific adsorption to *H. pylori* urease.

Glycoprotein-containing substances used in the present invention may be any glycoprotein-containing substance such as the milk of a mammal or the albumen, chalaza, vitelline membrane or yolk of eggs of a fowl. Preferably, the whey of bovine milk and the albumen of chicken eggs, particularly high-molecular-weight whey protein concentrate and high-molecular-weight albumen protein concentrate are used.

Glycoprotein is a conjugated protein in which sugar chains consisting of about 2–6 types of monosaccharides are bound covalently to proteins. It is distributed widely in organisms. The monosaccharides contained in glycoprotein are N-acetyl-D-glucosamine, N-acetyl-D-galactosamine, D-mannose, D-galactose, L-fucose, sialic acid, etc. There are various types of glycoproteins having different molecular weights and configurations. From the standpoint of forms of linkage between sugar chains and proteins, there are generally two types of glycoproteins, i.e., N-linked glycoproteins and O-linked glycoproteins (mucin type). Types of sugar chains, molecular weights and configurations of glycoproteins as well as functions or physiological activities vary depending on the location of glycoproteins existed.

Glycoproteins contained in bovine milk include lactoferin, secretory IgA, IgG, IgM, free secretory component (FSC), milk mucin and the like. Glycoproteins contained in the albumen of a chicken egg include ovomucoid, ovalbumin, ovotransferrin, phosvitin, ovomucin and the like.

In preparing a glycoprotein-containing substance, any known method can be used. A glycoprotein-containing substance may be prepared from bovine milk, for example, by removing milk fat and casein from milk in a conventional manner to obtain whey followed by fractional concentration of the whey by appropriate means such as ultrafiltration membrane treatment to obtain high-molecular-weight whey protein concentrate (glycoprotein-containing substance). A glycoprotein-containing substance may be also prepared by removing lipoprotein from the whey, optionally followed by concentration and dialysis, and subsequently purifying the resulting material by suitable means such as gel filtration using a Sepharose column, etc., and treatment with a membrane. Optionally, further treatment such as protease treatment, alkali hydrolysis, etc. may be performed in order to obtain low-molecular-weight glycoprotein. Bovine milk used in the present invention may be either colostrum or milk produced following colostrum.

A glycoprotein-containing substance may be prepared from the albumen of chicken eggs by the following procedures, for example. Thick albumen is separated from collected albumen. A gelatinous portion is recovered by ultracentrifugation and is solubilized by techniques such as ultrasonic wave treatment or homogenization. The resulting solubilized substance is treated by gel filtration, membrane treatment or any other techniques to obtain a glycoprotein-containing substance. The thus obtained glycoprotein-containing substance may be further purified, if necessary, by a procedure such as gel filtration.

A glycoprotein-containing substance from the mucous membrane or gel layer thereof in the alimentary canal may be usually recovered by solubilizing glycoprotein by homogenization or ultrasonic wave treatment and then isolating the high molecular weight fraction by gel filtration or ethanol precipitation. Solubilization of a glycoprotein-containing substance may be performed by extraction with guanidine hydrochloride, urea, a salt solution, or a surfactant or treatment with a reducing reagent or protease. Some kinds of glycoprotein-containing substances may be recovered by forming an insoluble complex with a quaternary ammonium salt or by precipitation under acidic conditions.

Advantageouly, bovine milk or the albumen of chicken eggs is used as a starting material of a glycoprotein-containing substance, since these materials can be obtained inexpensively and in large quantities, and the preparation of a glycoprotein-containing substance therefrom can be carried out easily and by a simple procedure. Also, in preparing a glycoprotein-containing substance from milk, milk whey can be used. In the past, milk whey has been discarded since there was no effective way of using it, although it is produced in large amounts as by-product during a process for preparing cheese and the like. Therefore, a glycoprotein-containing substance from whey can be prepared in large amounts industrially, and the use of a glycoprotein-containing substance from milk is very advantageous with respect to cost and practicality.

Additionally, glycoprotein in bovine milk or the albumen of chicken eggs is of high stability and does not lose its physiological activity due to heat or at a low pH, and therefore it can be readily recovered and purified from a starting material, and it is advantageous with respect to formulation into a food or medicament, processing, and storing.

Any method which utilizes specific adsorption to urease can be used for isolation and purification of glycoprotein which specifically binds to *H. pylori* urease from a glycoprotein-containing substance. Preferably, affinity chromatography using a column on which *H. pylori* urease is immobilized is used. As urease which is immobilized on a column, recombinant urease may be preferably used because of the availability of homogeneous urease in large amounts.

Recombinant urease may be prepared in a conventional way. For example, genomic DNA of *H. pylori* can be extracted, and a gene coding urease molecule can be amplified by PCR method to obtain amplified DNA, which can be subsequently integrated into expression vector for *E. coli* (e.g. pKK233-2) by a known method. The obtained vector can be incorporated into a suitable host, *E. coli* (e.g. *E. coli* XL1-Blue) to produce recombinants. The recombinants can be cultured in a suitable culture medium, thereby expressing urease. Recombinant urease can be obtained by recovering the expressed urease. In preparing recombinant urease, expression systems using yeasts, mammal cells and insect cells may be used. Procedures for preparing recombinant urease are described, for example, in Molecular Cloning, Laboratory Mannual (2nd ed.) (Cold Spring Harbor Press), and in DNA Cloning 2 (2nd ed.) (IRL Press).

Immobilization of urease on a column may be performed using a ligand-immobilizing carrier which is capable of binding an amino group (—NH$_3$), carboxyl group (—COOH), thiol group (—SH), or hydroxyl group (—OH) contained in urease (e.g. NHS-activated Sepharose 4 Fast Flow). Isolation and purification of glycoproteins by a urease-immobilized column may be carried out by passing a sample containing a glycoprotein-containing substance through this column, followed by washing away non-specifically adsorbed proteins, and then eluting glycoproteins, which have specifically adsorbed to urease, from the column with an appropriate eluting solution.

According to the above-mentioned method, only glycoprotein which specifically binds to urease can be isolated and purified efficiently from various types of glycoprotein-containg substances. The thus obtained glycoprotein can inhibit the adherence of urease produced by *H. pylori* to mucin of gastric mucosa as demonstrated in the following examples. Since urease is localized on the surface of *H. pylori* cells, the glycoprotein produced by the above-mentioned method which specifically binds to urease (hereinafter referred to as the glycoprotein of the present invention) masks the adhesin i.e., urease, by predominantly binding to urease in the stomach and thereby inhibits the adherence of *H. pylori* to the receptor on gastric mucosa. This was confirmed in animal experiments, and the effect of the glycoprotein of the present invention on elimination of *H. pylori* from the stomach was observed. Also, the glycoprotein of the present invention is naturally-occurring and is very safe. Therefore, the glycoprotein of the present invention can be used as an inhibitor of *H. pylori* colonization in the stomach and is useful for preventing or treating diseases caused by or associated with *H. pylori* such as peptic ulcers.

Accordingly, the glycoprotein of the present invention can be used as an inhibitor of *H. pylori* colonization to be formulated into a medicament or food. Especially, the glycoprotein from milk or albumen of chicken eggs has been eaten in the past, so it can be formulated into foods such as foods for specified health use having anti *H. pylori* activity, foods for special dietary uses including foods for the aged or foods for the ill, or dietary supplement foods or health foods having anti *H. pylori* activity.

When the glycoprotein of the present invention is added to foods to be used as foods for specified health use or as foods for special dietary uses, the glycoprotein may be added to foods, usually in an amount of about 0.005–0.5% by weight, and preferably 0.01–0.1% by weight of the food. Foods for specified health uses to which the glycoprotein of the present invention is added include milk, dairy products, meat products, mayonnaise, dressings, beverages, ice cream, tofu (soybean curd), daily dishes, tsukudani (preserved foods boiled down in soy sauce), bean jams, flour paste, instant noodles, powdered food to be sprinkled over rice, pickled vegetables, powdered soups, dehydrated soups, confections, canned foods, retort pouched foods, frozen foods, and the like. Among these, foods which can be consumed continuously are preferred, but not required. When added to foods for the ill such as low sodium food, low energy food, or low protein food, the glycoprotein of the present invention may be added to soups, beverages, liquid diets, etc. to prepare foods in various forms.

Dietary supplement foods may be prepared, for example by adding to the glycoprotein of the present invention excipients such as dextrin, adhesives such as sodium caseinate, and, if necessary, nutrients (e.g. vitamins, minerals), emulsifiers, stabilizers, flavors, and the like to prepare a liquid diet.

When the glycoprotein of the present invention is utilized as a heath food, the glycoprotein may be contained as an active ingredient in an amount of about 0.1–3% by weight of the food. The glycoprotein may be formulated together with excipients such as lactose, corn starch, crystalline cellulose, or PVP, or with binders, and optionally with nutrients such as vitamins and minerals to form various forms of foods such as fine particles, tablets, and granules.

The glycoprotein of the present invention can be used alone or along with conventional additives as a pharmaceutical composition for prevention or treatment of peptic ulcers, etc. The glycoprotein alone or along with additives may be formed by a conventional method into a preparation for oral administration such as tablets, granules, powders, capsules or liquid preparations. The additives which may be used include excipients, binder, disintegrators, lubricants, antioxidants, coloring materials, corrigents, and the like.

Excipients which can be used in a pharmaceutical composition include sodium carboxymethylcellulose, agar, light anhydrous silicic acid, gelatin, crystalline cellulose, sorbitol, talc, dextrin, starch, lactose, sucrose, glucose, mannitol, magnesium metasilicate aluminate, calcium hydrogenphosphate, and the like.

Binders which can be used include gum arabic, sodium alginate, ethanol, ethyl cellulose, sodium caseinate, sodium carboxymethylcellulose, agar, purified water, gelatin, starch, tragacanth, lactose, hydroxycellulose, hydroxymethycellulose, hydroxypropylcellulose, polyvinylpyrrolidon, and the like.

Disintegrators which can be used include carboxymethylcellulose, sodium carboxymethylcellulose, calcium carboxymethylcellulose, crystalline cellulose, starch, hydroxypropylstarch, and the like.

Lubricants which can be used include stearic acid, calcium stearate, magnesium stearate, talc, hydrogenated oil, sucrose fatty acid ester, wax, and the like.

Antioxidants which can be used include tocopherol, gallic acid ester, dibutyl hydroxy toluene (BHT), butyl hydroxy anisol (BHA), ascorbic acid, and the like.

Other additional additives or agents may be added if desired, such as antacids (e.g., sodium hydrogencarbonate, magnesium carbonate, precipitated calcium carbonate, synthetic hydrotalsite), agents for protection of gastric mucosa (e.g., synthetic aluminum silicate, sucralfate, and sodium copper chlorophyllin) and digestive enzymes (e.g., biodiastase or lipase). The administration of a pharmaceutical composition for prevention or treatment of peptic ulcers, etc. may be by an oral route. The dosage of the glycoprotein of the present invention will be usually 2–30 mg and preferably 5–20 mg (as a dry weight) per day for an adult.

Additionally, the above-mentioned pharmaceutical composition for prevention or treatment of peptic ulcers, etc.

may further comprise an inhibitor of gastric acid secretion. The combination of the glycoprotein and the inhibitor of gastric acid secretion is more effective in eliminating *H. pylori* from the stomach. Examples of an inhibitor of gastric acid secretion which can be used include $H_2$ blockers such as famotidine, nizatidine, roxatidine, ranitidine or cimetidine and proton pump inhibitors such as omeprazol, lansoprazol or sodium rabeprazole. The dosage of the inhibitor of gastric acid secretion is preferably 20–30 mg per day for an adult.

The following examples are given to further illustrate the present invention. It should be understood that the present invention is not limited to the specific details set forth in the examples.

EXAMPLE 1

(1) Preparation of Recombinant Urease of *H. pylori*

Genomic DNA of *H. pylori* strain TU130 was extracted, and the DNA coding urease molecule was amplified by the PCR method. The amplified DNA was integrated into expression vector pKK233-2 (Amersham Pharmacia Biotec) to obtain vectors to be used for expressing urease. The vector was incorporated into *E. coli* XL1-Blue to obtain *E. coli* capable of expressing urease. The recombinant bacteria were cultured with shaking at 100 rpm at 37° C. in 1.0 liter of LB medium containing 100 μg/ml of ampicillin. When the bacterial cells reached a logarithmic growth phase, isopropyl-β-D-thiogalactopyranoside (IPTG) was added at a concentration of 0.5 mM in order to induce expression, and the cells were further cultured with shaking overnight under the same conditions as above. The *E. coli* cells were harvested by centrifugation at 4,000×g for 20 minutes (+4° C.).

The obtained cells were suspended in tris buffer for lysis (50 mM Tri-HCl (pH 8.0), 100 mM NaCl, 1 mM EDTA). After addition of lysozyme at a concentration of 0.1 mg/ml, the suspension was allowed to stand in ice for 30 minutes. Then, the suspension was frozen at −80° C. for more than 1 hour, and was thawed at room temperature. The suspension was treated by ultrasonic wave, and Triton X-100 was added at a concentration of 1%. Inclusion bodies of recombinant urease were collected by centrifugation at 30,000×g for 30 minutes (+4° C.).

These inclusion bodies were suspended in a buffer for washing inclusion bodies (50 mM Tris-HCl (pH 8.0), 150 mM NaCl, 1 mM EDTA containing 0.1% SDS, 1.0% Triton X-100, 0.1% sodium deoxycholate) and centrifuged at 30,000×g for 10 minutes (+4° C.). The precipitated inclusion bodies were further washed twice in the same manner. These inclusion bodies were solubilized by suspending them in 8 M urea solution (8 M urea, 50 mM Tri-HCl (pH 8.0), 1 mM EDTA, 1 mM DTT) and then allowing the suspension to stand at room temperature for 1 hour. After the resulting suspension was centrifuged at 30,000×g for 30 minutes (+4° C.), the supernatant was dialyzed against 100-fold volume of 20 mM phosphate buffer supplemented with 1 mM EDTA (pH 6.5), thereby renaturating the configuration of urease to obtain recombinant urease-containing substance to be purified.

For purification of the above recombinant urease-containing substance, Cellulofine sulfate-m (Chisso Inc.) was equilibrated with 10 gel bed volumes of 20 mM phosphate buffer supplemented with 1 mM EDTA (pH 6.5). 50 ml of this substance readjusted to pH 6.5 was applied to the above Cellulofine sulfate-m equilibrated with 20 mM phosphate buffer supplemented with 1 mM EDTA (pH 6.5), and then 20 mM phosphate buffer (pH 6.5) supplemented with 1 mM EDTA was passed through the gel. Combined fractions having a peak containing urease were adjusted to pH 5.5 and were applied to Cellulofine sulfate-m preequilibrated with 10 gel bed volumes of 20 mM phosphate buffer supplemented with 1 mM EDTA (pH 5.5). After that, the gel was washed with 20 mM phosphate buffer (pH 5.5). Then, urease was extracted by passing 20 mM phosphate buffer, pH 7.4 containing 0.15 M NaCl through the gel. Combined fractions containing urease were dialyzed against a 100-fold volume of distilled water and were lyophilized to form powdered recombinant urease. The obtained recombinant urease were confirmed to be the same as natural urease of *H. pylori* by SDS-PAGE and western blotting.

(2) Preparation of Column Containing Immobilized Recombinant Urease of *H. pylori*

2 g of NHS-activated Sepharose 4 Fast Flow (Amersham Pharmacia Biotec Inc.) were suspended in about 50 ml of 1 mM HCl and were swelled at room temperature for 15 minutes. The swelled gel was subjectd to filtration with suction on a glass filter and washed twice with a 10-fold volume of 1 mM HCl. Then, the gel was suspended in 50 ml of coupling buffer (0.1 M $NaHCO_3$, 0.5 M NaCl, pH 8.8) and filtered with suction on a glass filter. 10 mg of powdered purified recombinant urease as prepared in above (1) were dissolved in 10 ml of coupling buffer. The resulting solution was immediately mixed with the gel, and was allowed to react overnight at 4° C. with gentle shaking by a shaker.

After the reaction mixture was removed by suction filtration, the resulting gel was suspended in blocking buffer (0.2 M glycine, pH 8.3) and was left overnight at 4° C. with gentle shaking to block the residual reactive groups. After the gel was filtered with suction on a glass filter, it was washed successively with 50 ml of coupling buffer, 50 ml of washing buffer (0.1 M acetic acid, 0.5 M NaCl, pH 4.0), and 100 ml of 20 mM phosphate buffer supplemented with 0.5 M NaCl (pH 7.0). The resulting gel was suspended in an approximately 5-fold volume of 20 mM phosphate buffer, pH 5.5 containing 0.5 M NaCl, which was directly poured into a column to fill it. The column was transferred to a low temperature room and was equilibrated with 3 bed volumes of 20 mM phosphate buffer, pH 5.5 containing 0.1 M NaCl, which is used as a column containing immobilized recombinant urease of *H. pylori* for isolating the glycoprotein of the present invention.

(3) Preparation of High-molecular-weight Whey Protein Concentrate from Bovine Milk Whey 20 liter of bovine milk was centrifuged at 2,000×g at 4° C. for 15 minutes so as to remove milk fat, and the supernatant was recovered. Then, to the supernatant, 1M acetic acid was added dropwise until the pH was 4.6 so as to remove casein. After the supernatant was allowed to stand for 1 hour at room temperature, casein was removed by centrifugation to obtain bovine whey. Then, the whey, which was adjusted to a pH of 6, was fractionated by ultrafiltration for 1000,000 Da to be concentrated to one-twentieth volume, and high-molecular-weight whey protein concentrate was obtained.

(4) Preparation of High-molecular-weight Albumen Protein Concentrate from Albumen of Chicken Eggs From 50 unfertilized eggs of White Leghorn hens within a week after being laid, only albumen was collected and was sieved to separate thick albumen, which was suspended in Mensel buffer (pH 9.5, ionic strength=0.01) and was solubilized by ultrasonic wave treatment at 10 W and 9 kHz (+2° C.) for 10 minutes. This solubilized product was fractionated by an ultrafiltration membrane for 300,000 Da of fractional molecular weight to be concentrated to one-twentieth volume, and high-molecular-weight albumen protein concentrate was obtained.

(5) Isolation of Urease Specifically-binding Glycoprotein Using Urease-immobilized Column One liter of each of the high-molecular-weight protein concentrates prepared in the above procedures (3) and (4) was adjusted to pH 5.5. The following procedures were conducted in a low temperature room. The urease-immobilized column prepared in the above procedure (2) was preequilibrated with 10 bed volumes of 20 mM phosphate buffer containing NaCl (pH 5.5). Each sample mentioned above was passed through this column. Then, the column was swept with 10 bed volume of 20 mM phosphate buffer containing 0.5 M NaCl (pH 5.5) to remove non-specifically adsorbed proteins. Glycoproteins which specifically had bound to urease in the column were eluted from the column with 20 mM phosphate buffer containing 0.5 M NaCl (pH 7.4). After dialysis with 100-fold distilled water followed by liophilization, the glycoprotein of the present invention, i.e., H. pylori urease-specifically binding glycoprotein was obtained approximately one gram at a time.

Experiment 1 In vitro Experiment

Inhibitory effects on adherence of urease produced by H. pylori to gastric mucosa were examined in an in vitro experiment system using high-molecular-weight whey protein concentrate prepared by the above-described procedure (3), high-molecular-weight albumen protein concentrate prepared by procedure (4), and the glycoprotein of the present invention prepared by procedure (5) of Example 1.

(Materials and Methods)

The present inventors had already found that an adhesin of H. pylori is urease produced by H. pylori. Since this urease binds well to mucin of gastric mucosa, porcine gastric mucin prepared as follows was used for urease adherence test.

Preparation of Porcine Gastric Mucin

Healthy pigs about two months old were slaughtered, and their stomachs were recovered and washed on the insides thereof with 0.1 M phosphate buffer (pH 7.4) containing 0.15M NaCl, 5 mM N-ethyl maleimide (NEM), 1 mM phenylmethylsulfonyl fluoride (PMSF) and 1 mM EDTA. The stomachs were incised, and the gastric mucosa was scraped and suspended in the above-mentioned buffer. This suspension of mucosa was homogenized by a Polytron homogenizer while being iced and was centrifuged at 15,000×g to recover a supernatant. The supernatant was centrifuged again at 25,000×g to recover a supernatant, which was dialyzed against distilled water and lyophilized to obtain crude gastric mucin. Then, this lyophilized crude gastric mucin was dissolved in 0.1 M phosphate buffer (pH 6.8) containing 0.15 M NaCl, 6M guanidine hydrochloride and protease inhibitor (5 mM NEM, 1 mM PMSF, 1 mM EDTA), and overlaid on a cesium chloride density gradient (1.5 g/ml) and centrifuged at 34,000×g for 48 hours. A sialic acid-containing fraction was detected by nitrocellulose membrane blotting and dyeing with periodic acid Schiffs reagent. Dyed fractions were pooled and overlaid on a cesium chloride density gradient and centrifuged. Dyeing-positive fractions were pooled and lyophilized. Then, the lyophilized product was subjected to gel filtration through a Sepharose CL-4 B column preequilibrated with 0. 1M phosphate buffer (0.1 M NaCl, pH 6.8) to carry out fractionation. Fractions which were PAS dyeing-positive and had proteins at a high concentration were pooled and dialyzed against PBS (pH 6.8) to obtain purified porcine gastric mucin, which was stored at −80° C. until use. The obtained gastric mucin was confirmed to be glycoprotein of 66kD by SDS-PAGE.

Urease Adherence Test to Porcine Gastric Mucin

A microplate for a urease adherence test was prepared as follows.

To each well of a 96-well microplate, a 50 µl portion of purified porcine gastric mucin (1.27 mg/ml) was added to each well and was subjected to immobilization by standing overnight at 4° C. When the microplate is used for urease adherence test, blocking is conducted by adding 3% BSA to each well to react at 37° C. for 60 minutes, and then the plate was washed three times with 20 mM phosphate buffer containing 0.15 M NaCl and 0.05% Tween 20.

A urease adherence test was carried out using the microplate prepared above in order to observe adherence of urease to porcine gastric mucin immobilized on the microplate, as follows.

Native urease prepared from H. pylori strain TU130 and recombinant urease prepared by procedure (1) of Example 1 were biotinylated and the biotinylated urease was diluted so as to give a final concentration of 7.0 µg/ml with adhesion media consisting of 20 mM phosphate buffer containing 0.15 M NaCl and 0.05% Tween 20 having different pH ranges (pH preadjusted to be 2.0, 3.0, 4.0, 4.5, 5.0, 5.5, 6.0 or 6.5). Each urease sample thus prepared was added to 2 wells of mucin-immobilized microplate mentioned above to conduct sensitization at 37° C. for 60 minutes. Then, in order to determine the amount of urease adhered to the well, streptoavidin HRP was added to each well to react at 37° C. for 60 minutes. Then, ortho-phenylenediamine 2HCl as a substrate and $H_2O_2$ were added to react. 3N $H_2SO_4$ was used for termination of the reaction. Known amounts of biotinylated urease diluted serially 2-fold were placed in a running plate and a calibration curve thereof was used to determine the amount of urease in a sample.

Inhibition Test of Urease Adherence

Inhibition tests of urease adherence were conducted using the glycoprotein of the present invention (Procedure (5) of Example 1), high-molecular-weight whey protein concentrate (Procedure (3) of Example 1), and high-molecular-weight albumen protein concentrate (Procedure (4) of Example 1). First, samples having various concentrations were each mixed with biotinylated porcine gastric mucin, and each mixture was transferred to a well of a 96-well plate immobilized with urease and sensitized at 37° C. for 60 minutes. Then, each well in the microplate was washed five times with adhesion medium (pH 4.0) and was fixed by heating at 65° C. for 10 minutes. The fixed wells were washed once with adhesion medium (pH 7.0), and streptoavidin HRP was added to each well to detect biotinylated porcine gastric mucin adhered to urease by ELISA as described above.

(Results)

Urease Adherence Pattern to Purified Pocine Gastric Mucin

As shown in FIG. 1, native urease and recombinant urease adhere specifically to porcine gastric mucin, and this adherence pattern depends on pH. Since urease adherence reaction at about pH 3.0 is considered to reflect the colonization characteristics of H. pylori in gastric mucosa, a substance which is able to inhibit the adherence of urease in this pH range may inhibit the colonization of H. pylori in the stomach. Since recombinant urease exhibits the same adherence properties as native urease, the glycoprotein of the present invention when purified using a column on which recombinant urease is immobilized is thought to inhibit the colonization of H. pylori in the stomach by masking urease of H. pylori.

Inhibition of Urease Adherence by Glycoprotein of the Present Invention

Figure 2:
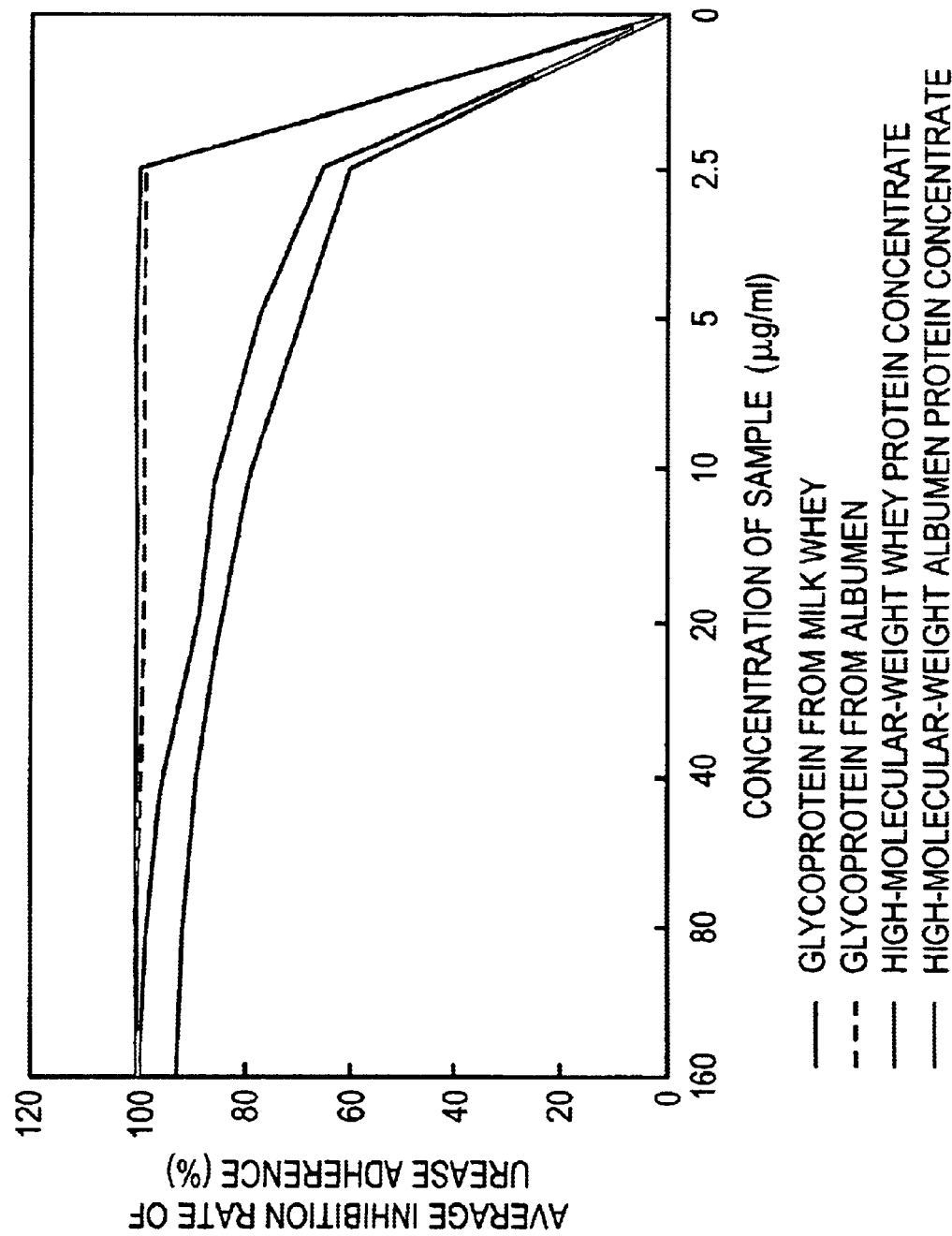
FIG. 2 is a graph showing the inhibition rate of urease adherence.

As shown in FIG. 2, urease adherence to porcine gastric mucin was inhibited dose-dependently with high-molecular-weight whey protein concentrate, high-molecular-weight albumen protein concentrate and the glycoprotein of the present invention purified from each of the protein concentrates. The glycoprotein of the present invention exhibited about 100% inhibitory activity even at a low concentration, which is a remarkably high efficacy. Urease is localized on the surface of *H. pylori* cells, and therefore the urease-binding glycoprotein of the present invention can inhibit infection with *H. pylori*, i.e., it can eliminate *H. pylori* from the stomach by binding to urease of the *H. pylori* cells and masking the urease, an adhesin, in the stomach.

Experiment 2 in vivo Experiment

This experiment was performed in an animal model to further confirm the results of Experiment 1.

(Method)

The experimental animals were hairless mice (NS:Hr/ICR, Research Institute for Human and Animal Propagation, Accession No. IRA-NHI-9701) (ATCC #72024) (Clin. Diagn. Lab. Immunol. 5: 578–582, 1998) having a high sensitivity to *H. pylori* infection. Each mouse was challenged with $1 \times 10^9$ CFU of strain NSP 335 by oral administration. After breeding for a week, the mice were administered the glycoproteins of the present invention added to feeds at various concentrations for 4 weeks. Another group was administered the glycoprotein of the present invention along with an $H_2$ blocker (famotidine) or a proton pump inhibitor (omeprazol). There were 10 mice in each group. After the completion of administration of the samples, the mice in each group were slaughtered. The stomachs of the mice were recovered, and after removal of the contents, the whole mucous membrane was homogenized by a homogenizer to form an emulsion, which was used for detection of *H. pylori*. The detection of *H. pylori* was carried out by placing the emulsion on a medium for detecting *H. pylori* (Poremedia *H. pylori* isolation medium, Eiken Kagaku), incubating at 37° C. for 5 days by the gas pack method, and counting colonies.

(Results)

Figure 3:
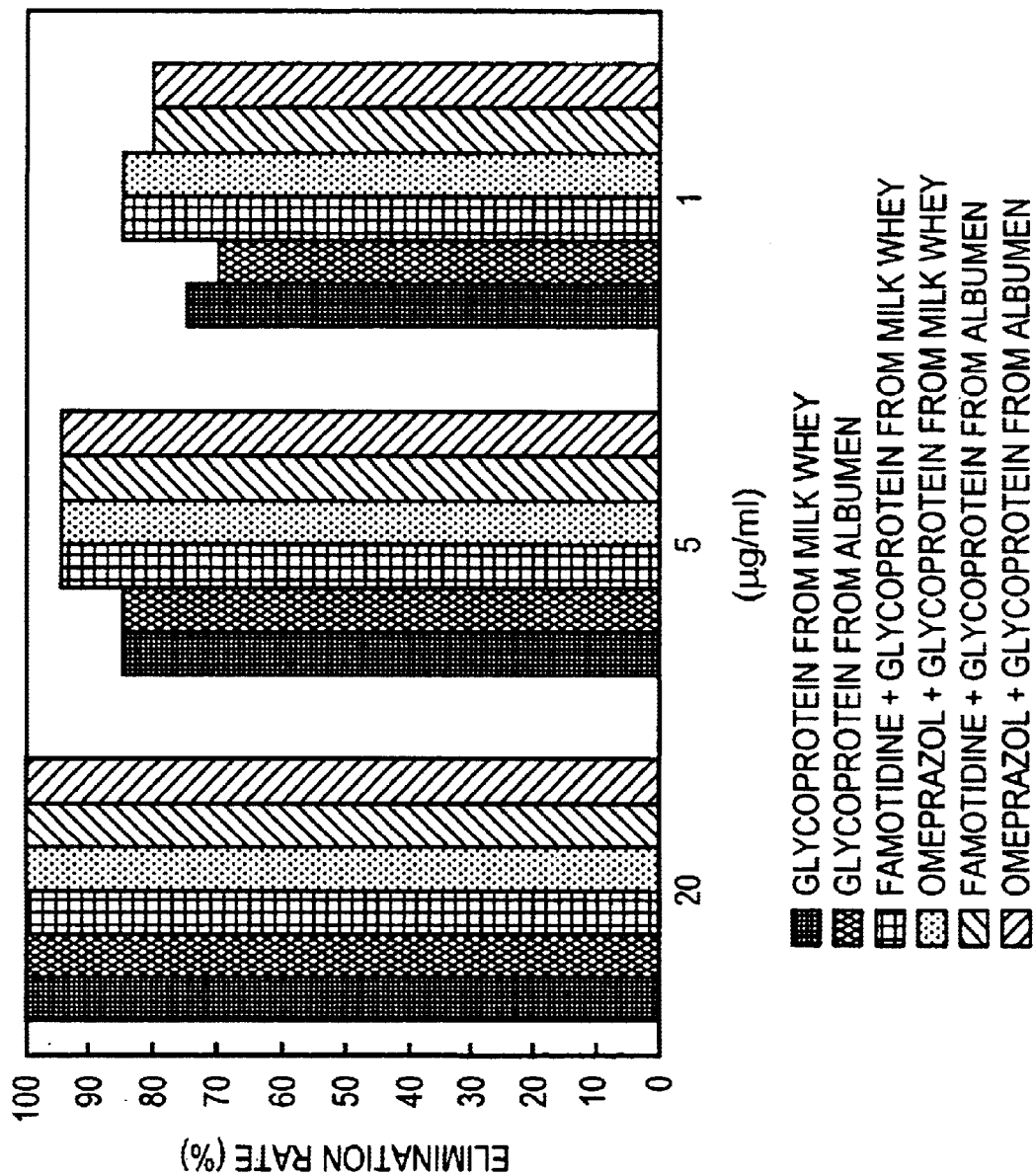
FIG. 3 is a graph showing the elimination rate of *H. pylori* in *H. pylori*-colonized mice.

Effects of Glycoprotein of the Present Invention on Elimination of *H. pylori* in *H. pylori*-colonized Mice As shown in FIG. 3, the glycoprotein of the present invention could eliminate *H. pylori* from the stomach in a concentration-dependent manner. The elimination rate was 100% at the maximum dose (20 μg/ml) and 70–75% at the minimum dose (1 μg/ml), which is remarkably high elimination rate corresponding to in vitro experiment results. 100% of mice (10/10) in the control group were infected with *H. pylori*. From these results, it is thought that the glycoprotein of the present invention can inhibit infection with *H. pylori* by binding predominantly to urease produced by *H. pylori* and masking the urease, an adhesin. Also, the combination of the glycoprotein and an inhibitor of gastric acid secretion showed enhanced efficacy.

Below, examples of various preparations are given. The glycoprotein used in the examples is the glycoprotein prepared by procedure (5) of Example 1.

Preparation 1 (Food)

| | |
|---|---|
| (Chewing gum) | |
| gum base | 25.0 |
| calcium carbonate | 2.0 |
| sorbitol | 54.0 |
| mannitol | 16.0 |
| flavor | 1.0 |
| glycoprotein | 1.0 |
| water q.s. to | 100.0 |
| | (% by weight) |
| (ice cream) | |
| cream (40% fat content) | 33.97 |
| milk (3.7% fat content) | 33.16 |
| defatted evaporated milk | 16.08 |
| sugar | 11.75 |
| corn syrup | 4.67 |
| stabilizer | 0.3 |
| glycoprotein | 0.02 |
| total | 100.0 |
| | (% by weight) |

Preparation 2
(Foods for special dietary uses)

| | |
|---|---|
| (powdered soup) | |
| powdered bean for cooking | 67.5 |
| wheat flour | 3.9 |
| wheat embryo | 2.5 |
| dry yeast powder | 2.5 |
| onion powder | 4.8 |
| meat extract powder | 15.5 |
| salt | 0.2 |
| spices (white pepper, etc.) | 1.8 |
| seasonings (amino acid, etc.) | 0.2 |
| glycoprotein | 0.1 |
| total | 100.0 |
| | (% by weight) |
| (dried soup) 10.0 g/200 ml | |
| chicken egg | 4.0 |
| meat extract | 1.3 |
| onion extract | 1.73 |
| carrot paste | 2.16 |
| kombu extract | 0.1 |
| emulsifier | 0.1 |
| salt | 0.2 |
| spice (red pepper) | 0.2 |
| seasonings (amino acid, etc.) | 0.2 |
| glycoprotein | 0.01 |
| total | 10.0 g |

Preparation 3 (Health Food)

Formula 1: in 100 g of fine particles

| | |
|---|---|
| glycoprotein | 1 g |
| lactose (200M) | 59 g |
| corn starch | 35 g |
| PVP (K-30) | 5 g |

These components were formulated into fine particles by a conventional wet granulation method.

Formula 2: in 100 g of Granules

| | |
|---|---|
| glycoprotein | 2 g |
| lactose (200 M) | 60 g |
| corn starch | 33 g |
| PVP (K-300) | 5 g |

These components were formulated into granules by a conventional extrusion granulation method.

Preparation 4
(Dietary supplement foods)

liquid food (200 ml/pack)

| | |
|---|---|
| glycoprotein | 0.01 |
| maltodextrin | 39.0 |
| casein Na | 13.0 |
| vegetable oil | 12.0 |
| vitamins | 1.0 |
| minerals | 1.5 |
| emulsifier | 0.2 |
| milk protein | 10.3 |
| sodium phosphate | 1.8 |
| potassium phosphate | 1.2 |
| flavor | 0.5 |
| stabilizer (carrageenan) | 1.5 |
| water q.s. to | 100.0 |
| | (% by weight) |

Tonic (soup type)

| | |
|---|---|
| glycoprotein | 0.02 |
| carrot (carrot paste) | 10.0 |
| heavy cream | 12.0 |
| lactose | 1.8 |
| onion (onion extract) | 1.5 |
| milk protein powder | 0.5 |
| milk oligosaccharide | 1.5 |
| consomme powder | 0.5 |
| wheat embryo | 0.5 |
| eggshell calcium | 0.2 |
| whey calcium | 0.1 |
| salt | 0.2 |
| emulsifier | 0.2 |
| water q.s. to | 100.0 |
| | (% by weight) |

Preparation 5 (Medicen)

Formula 1: in 1.5 kg of fine particles

| | |
|---|---|
| glycoprotein | 15 g |
| lactose | 1,100 g |
| corn starch | 340 g |
| PVP (K-30) | 45 g |

These components were granualated by a wet granulation method, followed by drying and forming into fine particles in a conventional way.

Formula 2: Tablets

| | |
|---|---|
| 1. glycoprotein | 15 g |
| 2. lactose | 400 g |
| 3. corn starch | 150 g |
| 4. crystalline cellulose | 210 g |
| 5. PVP (K-300) | 25 g |
| 6. magnesium stearate | 10 g |

The above components 1–5 were formulated into granules by a wet granulation method, magnesium stearate was then added to form powders for preparing tablets, and then these powders were compressed into tablets (200 mg/tablet).

Formula 3: in 1.5 kg of Granules

| | |
|---|---|
| glycoprotein | 20 g |
| lactose (200 M) | 950 g |

-continued

| | |
|---|---|
| corn starch | 480 g |
| PVP (K-30) | 50 g |

These components were mixed intimaftely and granulated by an extrusion granulation method, followed by drying and forming into granules in a conventional way.

Formula 4: in 1.5 kg of Fine Particles

| | |
|---|---|
| glycoprotein | 15 g |
| famotidine | 20 g |
| lactose | 1,100 g |
| corn starch | 320 g |
| PVP (K-30) | 45 g |

These components were granuled by a wet granulation method, followed by drying and forming into fine particles in a conventional way.

Formula 5: Tablets

| | |
|---|---|
| 1. glycoprotein | 20 g |
| 2. famotidine | 20 g |
| 3. lactose | 400 g |
| 4. corn starch | 135 g |
| 5. crystalline cellulose | 200 g |
| 6. PVP (K-300) | 25 g |
| 7. magnesium stearate | 10 g |

The above components 1–6 were formulated into granules by a wet granulation method, magnesium stearate was then added to form powders for preparing tablets, and then these powders were compressed into tablets (200 mg/tablet).

Formula 6: in 1.5 kg of Granules

| | |
|---|---|
| glycoprotein | 20 g |
| famotidine | 30 g |
| lactose (200M) | 950 g |
| corn starch | 450 g |
| PVP (K-30) | 50 g |

These components were granulated by an extrusion granulation method, followed by drying and forming into granules in a conventional way.

As is apparent from the above, in accordance with the present invention, a safe and effective inhibitor of *H. pylori* colonization and a food and medicament containing the inhibitor are provided. Since the glycoprotein which specifically binds to urease as an adhesin is isolated and purified from a glycoprotein-containing substance and used in the present invention, the adherence of *H. pylori* to gastric mucosa can be blocked effectively even when a small amount of the glycoprotein is used. Therefore, diseases caused by *H. pylori* such as peptic ulcers can be suppressed effectively without the occurrence of side effects. Unlike antibiotics which have been used for treatment of peptic ulcers, the glycoprotein of the present invention can eliminate *H. pylori* specifically from the stomach without producing drug-resistant bacteria. As a starting material of the glycoprotein of the present invention, milk and chicken eggs, which can be obtained inexpensively and in large amounts, may be used to prepare in a simple manner a glycoprotein which exhibits superior effects.

What is claimed is:

1. An inhibitor composition of *Helicobacter pylori* colonization, consisting essentially of a glycoprotein which is prepared by contacting a glycoprotein-containing substance from whey of bovine milk or albumen of chicken eggs with *Helicobacter pylori* urease and isolating and purifying the glycoprotein specifically bound to the urease.

2. A pharmaceutical composition for treating a gastrointestinal disease caused by *Helicobacter pylori* in mammals, comprising the inhibitor composition according to claim 1 and a pharmaceutically acceptable carrier.

3. An inhibitor composition of *Helicobacter pylori* colonization, comprising the inhibitor composition according to claim 1, and an inhibitor of gastric acid secretion.

4. A pharmaceutical composition for treating a gastrointestinal disease caused by *Helicobacter pylori* in mammals, comprising the inhibitor according to claim 1, an inhibitor of gastric acid secretion and a pharmaceutically acceptable carrier.

5. A process for preparing a glycoprotein which specifically binds to urease of *Helicobacter pylori*, comprising contacting a glycoprotein-containing substance from whey of bovine milk or albumen of chicken eggs with *Helicobacter pylori* urease and isolating and purifying the glycoprotein specifically bound to the urease.

6. The process according to claim 5, wherein said contacting step involves affinity chromatography using a column on which the urease is immobilized.

7. A process for preparing a glycoprotein as an inhibitor of *Helicobacter pylori* colonization, comprising contacting a glycoprotein-containing substance from whey of bovine milk or albumen of chicken eggs with *Helicobacter pylori* urease and isolating and purifying the glycoprotein specifically bound to the urease.

8. The process according to claim 7, wherein said contacting step involves affinity chromatography using a column on which the urease is immobilized.

9. The inhibitor composition according to claim 1, wherein said contacting step involves affinity chromatography using a column on which the urease is immobilized.

10. The inhibitor composition according to claim 9, wherein the urease immobilized on the column is recombinantly produced.

11. The inhibitor composition according to claim 1, wherein the glycoprotein-containing substance is high molecular weight whey concentrate.

12. The inhibitor composition according to claim 1, wherein the glycoprotein-containing substance is high molecular weight albumen protein concentrate.

13. A method for inhibiting *Helicobacter pylori* colonization in mammals, comprising orally administering to said mammal a glycoprotein which specifically binds to urease of *Helicobacter pylori* in an effective amount for inhibiting *Helicobacter pylori* colonization, wherein the glycoprotein is obtained by contacting a glycoprotein-containing substance from whey of bovine milk or albumen of chicken eggs with *Helicobacter pylori* urease and isolating and purifying the glycoprotein specifically bound to the urease.

14. A method for inhibiting *Helicobacter pylori* colonization in mammals, comprising orally administering to said mammal a glycoprotein which specifically binds to urease of *Helicobacter pylori* and an inhibitor of gastric acid secretion in an effective amount for inhibiting *Helicobacter pylori* colonization, wherein the glycoprotein is obtained by contacting a glycoprotein-containing substance from whey of bovine milk or albumen of chicken eggs with *Helicobacter pylori* urease and isolating and purifying the glycoprotein specifically bound to the urease.

15. A method for treating a gastrointestinal disease caused by *Helicobacter pylori* in mammals, comprising orally administering to said mammal a glycoprotein which specifically binds to urease of *Helicobacter pylori* in an effective amount for treating the disease by inhibiting *Helicobacter pylori* colonization, wherein the glycoprotein is obtained by contacting a glycoprotein-containing substance from whey of bovine milk or albumen of chicken eggs with *Helicobacter pylori* urease and isolating and purifying the glucoprotein specifically bound to the urease.

16. A method for treating a gastrointestinal disease caused by *Helicobacter pylori* in mammals, comprising orally administering to said mammal a glycoprotein which specifically binds to urease of *Helicobacter pylori* and an inhibitor of gastric acid secretion in an effective amount for treating the disease by inhibiting *Helicobacter pylori* colonization, wherein the glycoprotein is obtained by contacting a glycoprotein-containing substance from whey of bovine milk or albumen of chicken eggs with *Helicobacter pylori* urease and isolating and purifying the glycoprotein specifically bound to the urease.

* * * * *